(12) United States Patent
Miyake et al.

(10) Patent No.: US 8,778,882 B2
(45) Date of Patent: Jul. 15, 2014

(54) AGENT FOR STRENGTHENING CALCIUM CONTAINING TISSUE AND USE THEREOF

(75) Inventors: Masaki Miyake, Okayama (JP);
Shimpei Ushio, Okayama (JP); Kanso Iwaki, Okayama (JP); Masashi Kurimoto, Okayama (JP)

(73) Assignee: Hayashibara Co., Ltd., Okayama (JP)

( * ) Notice: Subject to any disclaimer, the term of this patent is extended or adjusted under 35 U.S.C. 154(b) by 440 days.

(21) Appl. No.: 12/210,587

(22) Filed: Sep. 15, 2008

(65) Prior Publication Data

US 2009/0075908 A1 Mar. 19, 2009

Related U.S. Application Data

(62) Division of application No. 10/513,119, filed as application No. PCT/JP02/04407 on May 2, 2002, now abandoned.

(30) Foreign Application Priority Data

May 1, 2002 (JP) .................................. 2002-130154

(51) Int. Cl.
*A61K 38/00* (2006.01)
*A61P 19/10* (2006.01)
*A01N 43/16* (2006.01)
*A61K 31/35* (2006.01)

(52) U.S. Cl.
USPC ......................................... 514/16.9; 514/456

(58) Field of Classification Search
None
See application file for complete search history.

(56) References Cited

U.S. PATENT DOCUMENTS

| 5,478,579 A | 12/1995 | Sawruk |
| 5,525,618 A | 6/1996 | Shudo et al. |
| 5,627,157 A * | 5/1997 | Hijiya et al. ..................... 514/25 |
| 6,117,429 A * | 9/2000 | Bucci ............................ 424/729 |
| 6,203,818 B1 * | 3/2001 | Vester ........................... 424/569 |
| 6,297,273 B1 | 10/2001 | Romanczyk, Jr. |
| 2002/0015722 A1 | 2/2002 | Herzog et al. |

FOREIGN PATENT DOCUMENTS

| EP | 0 906 761 A2 | 4/1999 |
| EP | 1 025 850 A1 | 8/2000 |
| EP | 1 127 572 A2 | 8/2001 |
| JP | 63-156720 A | 6/1988 |
| JP | 63-156721 A | 6/1988 |
| JP | 63-156722 A | 6/1988 |
| JP | 63-156723 A | 6/1988 |
| JP | 63-201123 A | 8/1988 |
| JP | 63-201124 A | 8/1988 |
| JP | 11-009221 A | 1/1999 |
| JP | 2000-080035 A | 3/2000 |

(Continued)

OTHER PUBLICATIONS

Head, Kathleen, Ipriflavone: An Important Bone-Building Isoflavone, 1999, Alternative Medicine Review, vol. 4, No. 1, pp. 10-22.*

(Continued)

*Primary Examiner* — Trevor Love
(74) *Attorney, Agent, or Firm* — Browdy and Neimark, PLLC (57) ABSTRACT

The present invention has an object to provide an agent for strengthening calcium-containing tissues, which can be safely applied; and its use: The present invention solves the object by providing an agent for strengthening calcium-containing tissues, which comprises one or more flavones, flavonols, flavanones, flavanonols, anthocyanidins, flavanols, chalcones, and aurones.

2 Claims, 2 Drawing Sheets

(56) References Cited

FOREIGN PATENT DOCUMENTS

| | | | |
|---|---|---|---|
| JP | 2001-072582 A | 3/2001 | |
| JP | 2001-114675 A | 4/2001 | |
| WO | WO 99/65337 | 12/1999 | |
| WO | WO00/02553 * | 1/2000 | ............. A61K 31/35 |
| WO | WO 01/15553 A1 | 3/2001 | |
| WO | WO 01/91734 A2 | 12/2001 | |

OTHER PUBLICATIONS

Datta, et al, Osteopetrorickets, 2000, Indian Pediatrics, 37, pp. 98-99, pp. 1-3 printed from http://www.indianpediatrics.net/jan2000/case5.htm. 3 pages in all.*

Nishizaki et al., "Disaccharide-Trehalose Inhibits Bone Resorption in Ovariectomized Mice," 2000, Nutrition Research, vol. 20, No. 5, pp. 653-664.

* cited by examiner

AGENT FOR STRENGTHENING CALCIUM CONTAINING TISSUE AND USE THEREOF

CROSS-REFERENCE TO RELATED APPLICATIONS

The present application is a divisional of Ser. No. 10/513,119, filed Nov. 1, 2004 now abandoned, which claims priority from JP 130154/2002 and PCT/JP02/04407, filed May 2, 2002.

TECHNICAL FIELD

The present invention relates to an agent for strengthening calcium-containing tissues, which is usable to increase calcium contents in tissues such as bone and tooth, as well as to its use.

BACKGROUND ART

Aging usually weakens calcium-containing tissues such as bone and tooth. Bone tissues undergo without cease the formation and absorption of bone which are kept in an adequate balance in younger living bodies. Such a balance may be lost by a variety of causes such as unbalanced hormone secretion which is caused by extreme diet and aging, resulting in an excessive bone absorption. If such a state prolongs, then calcium-containing tissues such as bone and tooth loose calcium, one of their important elements, and this may accelerate the incidence of bone disorders such as osteoporosis, bone break and backache, as well as of tooth disorders such as dental caries and periodontosis.

Calcium in living bodies is present in a calcium phosphate solid such as hydroxyapatite: It plays an important role in the formation of bone and tooth and strengthening their tissues, as well as functioning as a source for calcium ion which is indispensable for living bodies. It is said that Japanese people may be lack for calcium intake, and this has triggered the commercialization of various health foods directed to supplement calcium. The way of supplementing calcium however should be carefully chosen because calcium intake may be ineffective due to its less assimilativity, as well as because an excessive intake may cause hypercalcemia. Because of these, it has been recommended that in order to deposit calcium in tissues, calcium is intaken as nutrient, then other minerals such as magnesium is intaken to accelerate the assimilativity and metabolism of calcium. This however has been proved insufficient for effectiveness. With the same purpose, lipid soluble vitamins and hormones such as vitamin D, calcitonin, estrogen, protein anabolic hormone and bisphosphonate are administered together with these minerals. The method however has not been proved satisfiable: It may be more effective than sole intake of calcium but lead to complicated administration schedule for lipid-soluble vitamins and hormones when such a vitamin or hormone is used because their excessive administration is causative of undesirable side effects.

The present invention is to provide a non-toxic agent for strengthening calcium-containing tissues with safeness, as well as to provide its uses including foods, cosmetics and pharmaceuticals to which such agent is incorporated.

DISCLOSURE OF THE INVENTION

The present inventors eagerly screened plant substances, leading to an unexpected finding that a series of compounds having the basic structure represented by any one of General Formulae 1 to 5 as described hereafter and their precursors (referred to as "compounds of General Formulae 1 to 5" hereinafter) consistently leads the calcium metabolism system in animals towards calcium deposition to accelerate the deposition of calcium in calcium-containing tissues and also strengthen them, thus increasing bone mass. Further, it was found that isoflavones leads the calcium metabolism system in animals towards calcium deposition to accelerate the deposition of calcium in calcium-containing tissues and strengthen them when used together with the compounds of General Formulae 1 to 5, thus increasing bone mass. These led to the present invention.

Particularly, the present invention is to provide an agent for strengthening calcium-containing tissues, which comprises as effective ingredient one or more compounds of General Formulae 1 to 5, for example, flavones, flavonols, flavanones, flavanonols, anthocyanidins, flavanols, chalcones, aurones and their precursors.

Further the present invention is to provide an agent for strengthening calcium-containing tissues, which contains isoflavones together with the above described compounds.

Still further, the present invention is to provide the use in foods, beverages, cosmetics and pharmaceuticals to which the above described agent is incorporated.

BEST MODE FOR CARRYING OUT THE INVENTION

The following will explain several embodiments according to the present invention: Compounds of General Formulae 1 to 5 feasible in the present invention are substances classified into "flavonoid" or a plant ingredient with an extended distribution. Compounds with a basic structure of General Formula 1 are designated as either flavone, flavonol, flavanone, or flavanonol: flavones characterized in that $R_1$ is hydrogen atom and "X", a double bond; flavonols characterized in that $R_1$ is hydroxy group (where hydroxy group may be glycosylated with saccharide) and X, a double bond; flavanones characterized in that $R_1$ is hydrogen atom and X, a single bond; and flavanonols characterized in that $R_1$ is hydroxy group (where hydroxy, group may be glycosylated with saccharide) and X, a single bond. In the present invention, substances as listed in Table 1 are feasible as compound with the basic structure of General Formula 1: In Table 1, "H" means hydrogen atom; "OH", hydroxy group; "OCH$_3$", methoxyl group; "OGlu", a glycosylated glucose; "ORha", a glycosylated rhamnose; and "ORut", a glycosylated rutinose.

General Formula 1 where "X" is a single or double bond, while $R_1$ to $R_{10}$ may be substituents,

TABLE 1

|  | Substance Name | $R_1$ | $R_2$ | $R_3$ | $R_4$ | $R_5$ | $R_6$ | $R_7$ | $R_8$ | $R_9$ | $R_{10}$ | *X |
|---|---|---|---|---|---|---|---|---|---|---|---|---|
| Flavones | Flavone | H | H | H | H | H | H | H | H | H | H | W |
|  | Chrysin | H | OH | H | OH | H | H | H | H | H | H | W |
|  | Apigenin | H | OH | H | OH | H | H | H | OH | H | H | W |
|  | Luteolin | H | OH | H | OH | H | H | OH | OH | H | H | W |
|  | Acacetin | H | OH | H | OH | H | H | H | $OCH_3$ | H | H | W |
|  | Linarin | H | OH | H | ORut | H | H | H | $OCH_3$ | H | H | W |
| Flavonols | Flavonol | OH | H | H | H | H | H | H | H | H | H | W |
|  | Kaempferol | OH | OH | H | OH | H | H | H | OH | H | H | W |
|  | Quercetin | OH | OH | H | OH | H | H | OH | OH | H | H | W |
|  | Morin | OH | OH | H | OH | H | OH | H | OH | H | H | W |
|  | Myricetin | OH | OH | H | OH | H | H | OH | OH | OH | H | W |
|  | Quercetagetin | OH | OH | OH | OH | H | H | OH | OH | H | H | W |
|  | Isorhamnetin | OH | OH | H | OH | H | H | $OCH_3$ | OH | H | H | W |
|  | Astragarin | OGlu | OH | H | OH | H | H | H | OH | H | H | W |
|  | Quercitrin | ORha | OH | H | OH | H | H | OH | OH | H | H | W |
|  | Rutin | ORut | OH | H | OH | H | H | OH | OH | H | H | W |
|  | Myricitrin | ORha | OH | H | OH | H | H | OH | OH | OH | H | W |
| Flavanones | Flavanone | H | H | H | H | H | H | H | H | H | H | S |
|  | Naringenin | H | OH | H | OH | H | H | H | OH | H | H | S |
|  | Sakuranetin | H | OH | H | $OCH_3$ | H | H | H | OH | H | H | S |
|  | Hesperetin | H | OH | H | OH | H | H | OH | $OCH_3$ | H | H | S |
|  | Eriodictyol | H | OH | H | OH | H | H | OH | OH | H | H | S |
|  | Sakuranin | H | OGlu | H | $OCH_3$ | H | H | H | OH | H | H | S |
|  | Naringin | H | OH | H | ORha | H | H | H | OH | H | H | S |
|  | Hesperidin | H | OH | H | ORut | H | H | OH | $OCH_3$ | H | H | S |
| Flavanonols | Fustin | OH | H | H | OH | H | H | OH | OH | H | H | S |
|  | Taxifolin | OH | OH | H | OH | H | H | OH | OH | H | H | S |

*"W" means a double bond and "S" means a single bond.

Compounds of General Formula 2 are designated as anthocyanidins. In the present invention, substances as listed in Table 2 can be used: In the Table 2, "H" means hydrogen atom; "OH", hydroxy group; "$OCH_3$", methoxyl group; "OGlu", a glycosylated glucose.

Compounds of General Formula 3 are designated as flavanols. In the present invention, substances as listed in Table 3 can be used: In the Table 3, "H" means hydrogen atom; "OH", hydroxy group.

General Formula 2 wherein $R_1$ to $R_{10}$ may be substituents.

General Formula 3 wherein $R_1$ to $R_{10}$ may be substituents.

TABLE 2

| Substance Name | $R_1$ | $R_2$ | $R_3$ | $R_4$ | $R_5$ | $R_6$ | $R_7$ | $R_8$ | $R_9$ | $R_{10}$ |
|---|---|---|---|---|---|---|---|---|---|---|
| Cyanidin | OH | OH | H | OH | H | H | OH | OH | H | H |
| Pelargonidin | OH | OH | H | OH | H | H | H | OH | H | H |
| Delphinidin | OH | OH | H | OH | H | H | OH | OH | OH | H |
| Peonidin | OH | OH | H | OH | H | H | H | OH | $OCH_3$ | H |
| Malvidin | OH | OH | H | OH | H | H | $OCH_3$ | OH | $OCH_3$ | H |
| Malvidin-3-Glucoside | OGlu | OH | H | OH | H | H | $OCH_3$ | OH | $OCH_3$ | H |

TABLE 3

| Substance Name | R₁ | R₂ | R₃ | R₄ | R₅ | R₆ | R₇ | R₈ | R₉ | R₁₀ |
|---|---|---|---|---|---|---|---|---|---|---|
| Catechin | OH | OH | H | OH | H | H | H | OH | OH | H |
| Epicatechin | OH | OH | H | OH | H | H | OH | OH | H | H |
| Epigallocatechin | OH | OH | H | OH | H | H | OH | OH | OH | H |

Compounds of General Formula 4 are designated as chalcones. In the present invention, substances listed in Table 4 can be used: In the Table 4, "H" means hydrogen atom, "OH", hydroxy group.

General Formula 4 wherein $R_1$ to $R_{11}$ may be substituents

TABLE 4

| Substance Name | R₁ | R₂ | R₃ | R₄ | R₅ | R₆ | R₇ | R₈ | R₉ | R₁₀ | R₁₁ |
|---|---|---|---|---|---|---|---|---|---|---|---|
| Chalcone | H | H | H | H | H | H | H | H | H | H | H |
| Phloretin | H | OH | H | OH | H | H | H | OH | H | H | OH |

Compounds of General Formula 5 are designated as aurones. In the present invention, substances as listed in Table 5 can be used: In the Table 5, "H" means hydrogen atom; "OH", hydroxy group; "OCH₃", methoxyl group.

General Formula 5 wherein $R_2$ to $R_{10}$ may be substituents.

TABLE 5

| Substance Name | R₂ | R₃ | R₄ | R₅ | R₆ | R₇ | R₈ | R₉ | R₁₀ |
|---|---|---|---|---|---|---|---|---|---|
| Sulfuretin | H | H | OH | H | H | OH | OH | H | H |
| Leptosidin | H | H | OH | OCH₃ | H | OH | OH | H | H |

The compounds of General Formulae 1 to 5, which are feasible in the present invention, are flavones, flavonols, flavanones, flavanonols, anthocyanidins, flavanols, chalcones, aurones, or their precursors usually in the form of an a glycon or glycoside. One can choose any derivatives such as polymers of natural origin; and any precursors which are free of the basic structure represented by General Formulae 1 to 5 but changeable into any one of the compounds of General Formulae 1 to 5 during ingestion and subsequent metabolization in vivo, as long as they are capable of enhancing, the calcium level in calcium-containing tissues. As to such compound, there are available proanthocyanidin which is a precursor of cyanidin, a type of anthocyanidins, and proanthocyanidin polymer or persimmon tannin which is a polymer of proanthocyanidin. The compounds of General Formulae 1 to 5 and their derivatives are used in the form of, for example, an intact or purified extract, regardless of its purity and origin: Such extract can be obtained by subjecting a plant material with a higher compound content to extraction in an appropriated solvent, and further to purification to elevated the purity, if necessary. Also feasible are those which are synthesized in an artificial manner, and commercialized products. Such compound may be used in the form of a derivative which is subjected to a methylated, ethylated, methoxylated, ethoxylated, sulfated, or glycosylated derivative produced by a proper chemical or biochemical method, or soluble and/or stable derivatives thereof conjugated with an aqueous polymer such as polyethyleneglycol. As such derivatives, for example, α-glucosyl rutin (product name "αG RUTTIN", commercialized by Hayashibara Shoji Inc., Okayama, Japan), α-glucosyl hesperidin (product name "αG HESPERIDIN", commercialized by Hayashibara Shoji Inc., Okayama, Japan), methylated hesperidin (Alpus Pharmaceutical Industry Corporation, Gifu, Japan), α-glycosyl quercetin, and α-gycosyl narindin are listed. When an insoluble compound uses, as necessary, it can be dissolved in appropriate solvent such as dimethyl sulfoxide and ethanol, optionally with trehalose, or prepared as a suspension as long as the effects of the present invention are exerted.

The compounds of General Formulae 1 to 5, which are feasible in the present invention, in combination with isoflavoves known to have osteoporosis-treatment/prevention effect remarkably enhance the action of strengthening calcium-containing tissues in a synergic manner. The term "isoflavones" is a generic name for the compounds of having a structure represented by General Formula (3

The compounds are usually in the form of an aglycon or glycoside.

For example, such compounds are listed in Table 6, and they can be advantageously incorporated into the agent of the present invention.

Any isoflavone can be used in the present invention as long as it further enhances the effect of the compounds of General Formulae 1 to 5 on strengthening calcium-containing tissues.

For example, an intact or purified extract, regardless of its purity or origin: Such extract can be obtained by subjecting a plant material with a higher compound content to extraction in an appropriate solvent, and further to purification to elevate the purity, if necessary. Soybean isoflavone is example of such isoflavone. Also feasible are those which are synthesized in an artificial manner, and commercialized products. When an insoluble compound uses, as necessary, it can be dissolved in appropriate solvent such as dimethyl sulfoxide and ethanol, optionally with trehalose, or prepared as a suspension as long as the effects of the present invention are exerted. Such compounds may be used in the form of a derivative which is subjected to a methylated, ethylated, methoxylated, ethoxylated, sulfated, or glycosylated derivative produced by a proper chemical or biochemical method, or soluble and/or stable derivatives thereof conjugated with an aqueous polymer such as polyethyleneglycol, Example of above derivative is an α-isoglycosylisoflavone.

General Formula 6 wherein $R_1$ to $R_{10}$ may be substituents.

TABLE 6

| Compound Name | $R_1$ | $R_2$ | $R_3$ | $R_4$ | $R_5$ | $R_6$ | $R_7$ | $R_8$ | $R_9$ | $R_{10}$ |
|---|---|---|---|---|---|---|---|---|---|---|
| Ipriflavone | H | H | H | $OC_3H_7$ | H | H | H | H | H | H |
| Genistein | H | OH | H | OH | H | H | H | OH | H | H |
| Daidzein | H | H | H | OH | H | H | H | OH | H | H |
| Genistin | H | OH | H | OGlu | H | H | H | OH | H | H |
| Daidzin | H | H | H | OGlu | H | H | H | OH | H | H |

The term "calcium-containing tissues" as referred to in the present invention means tissues in general which are abundant for crystal calcium solid, for example, potassium phosphate salt including hydroxyapatite. Bone and tooth tissues are illustrative for such a tissue. The agent of the present invention effectively strengthens these calcium-containing tissues.

The agent of the present invention may further contain other ingredients for example, excipient such as anhydrous silicate, synthesized aluminum silicate, lactose, α,α-trehalose, α,β-trehalose, gum Arabic, corn starch, and crystalline cellulose, binder such as carboxymethyl cellulose and polyvinyl pyrrolidone, lubricant such as magnesium stearate and talc, disintegrant such as starch and carboxymethyl cellulose calcium, solvent such as water and ethanol, in addition to the compounds of General Formulae 1 to 5 or the compounds and isoflavones as effective ingredients, if necessary, the present agent can be prepared together with such an additional ingredient into powder, granule, tablet, liquid, paste or suspension. Particularly, since as disclosed in Japanese Patent Kokai Nos. 38,343/00 and 198,736/00, α,α-trehalose is useful for treatment or prevention of osteoporosis, it can be advantageously used in the present invention.

The compounds of General Formulae 1 to 5 can be used in the present invention alone or in combination with isoflavones and/or any pharmaceutically acceptable carrier or diluent. The effective ingredient according to the present invention is incorporated to give a concentration of 0.0001% (w/w) or more, desirably 0.001% (w/w) or more, on a dry solid basis. The agent can be administered through oral or parenteral route. Any administration routes can be employed in the present invention, as long as the present agent exhibits prescribed effects with such an administration route. Therefore the present invention provides no limitations for administration dose: However, it is usually administered in an amount of 0.1-500 mg/kg body weight/day, preferably 0.5-200 mg/kg body weight/day for the effective ingredients while in human dividing such a dose by several times.

Many of the compounds of General Formulae 1 to 5 as the effective ingredient in the agent according to the present invention have been proved safe because they have been used as additive for foods, cosmetic materials, or pharmaceutical materials. Therefore, the compounds can be prepared into foods, beverages, cosmetics, or pharmaceuticals which are administered, taken or used as the agent for strengthening calcium-containing tissues with safeness.

The agent of the present invention is applicable to any animals, for example, vertebrates including human and non-human mammals which bear bone or tooth tissues containing calcium solid as basic ingredient.

The agent of the present invention exhibits the prescribed effects in the treatment, acceleration of recovery, or prevention of bone disorders such as osteoporosis and bone break, tooth disorders such as dental caries and decay of the alveolar bone due periodontosis. Further, it can be used in the prevention of bone loss due to bone absorption or the decalcification caused by side effects of drugs such as hormones or cytokines which may be administered in the treatment of other diseases, as well as in the facilitation of rooting natural or artificial bones. The present agent is useful in the prevention of bone loss in healthy person because various factors induce bone loss even in healthy person. The present agent is effective in the treatment and prevention of any bone loss due to other causes, for example, postmenopausal or before-and-after childbirth hormone secretion disorders in women, excessive dietary or malnourish; lack of physical exercise in aged person, bedridden person such as acropalaysis and long-term inpatient, residence with no or less gravity such as those in the space or water, or excessive exercise. Further the present agent effectively accelerates bone-growth in infants, as well as maintaining an appropriated, bone mass in aged person. Still further, the presented agent would be expected to improve hypercalcemia because it accelerates to deposition of blood plasma calcium in calcium-containing tissues. These effects have no limitation to human, thus the present agent is applicable to any vertebrates including dog, cat, cow, pig, horse, deer, rhinoceros, elephant, and razorback.

The agent of the present invention may exhibit higher effects when an effective amount of the agent is used in combination with conventional drugs for treatment of osteoporosis Examples of such a conventional drug are calcitonin preparation, estrogen preparation, bisphosphonate preparation, vitamin D preparation, and vitamin K preparation. The present agent can be used in combination with anesthetics, hypnotic sedatives, anti-anxieties, antiepileptics, antipyretic antiphlogistics, stimulants, wake amines, antiparkinson drugs, agents for psychoneuroses, agents for central nervous system, skeletal muscle relaxants, agents for autonomic nervous system, antispastic agents, drugs for eye, drugs for nose and ear, anti-vertiginous drugs, cardiotonics, antiarrhythmic drugs, diuretics, pressure reduction drugs, vasoconstrictors, coronary vaso-dilators, peripheral vasodilating drugs, hyperlipemia drugs, breath stimulants, antitussive and expectorant drugs, bronchodilators, drugs for allergy, antidiarrheal drugs, drugs for intestinal disorders, peptic ulcer drugs, stomachic digestants, antacids, cholagogues, pituitary hormone drugs, salivary gland hormones, thyroid hormone drugs, antithyroid drugs, anabolic steroids, corticosteroids, androgen drugs, estrogen drugs, corpus luteum hormone drugs, mixed hormones, urinary/genital organ drugs, anus drugs, surgical sterilizations/antiseptics, wound protectives, externals for purulent diseases, analgesics, antipruritics, astringents, antiphlogistics, externals for parasite skin diseases, skin-softening drugs, caustics, dental/oral drugs, vitamins, inorganic preparations, supplemental liquids, hemostatics, anticoagulation drugs, drugs for liver diseases; antidotes, habitual intoxication drugs, drugs for treatment of gout, enzyme preparations, diabetic drugs, antioncotics, antihistaminics, drugs for stimulation treatment, antibiotics, chemotherapeutics, biological preparations, anthelmics, anti-protozoas, drugs for preparations, X-ray contrast media, and diagnostic drugs which are commonly used in the art. In addition, the agent of the present invention can be prepared in the form of extracts, elixirs, capsules, granules, pills, ointments for eye, suspensions, emulsions, plasters, suppositories, powders, ethanol preparations, tablets, syrups, infusions, decoctions, injections, tinctures, ophthalmic solutions, trochees, ointments, cataplasms, aromatic water, liniments, lemonades, fluidextracts, lotions, drinks, nasal drops, nasal nebulas, inhalants for lower airway, sustained-release drops for eye, oral mucosal patches, and enemas by adding with one or more agents which enable easily taking the agent of the present invention such as coadjuvants, fillers, diluents, excipients, stabilizers, antiseptics, coloring agents, or flavoring agents.

The agent of the present invention can be prepared by subjecting a prescribed amount of the effective ingredient to blending, kneading, resolving, immersing, diffusing, applying, spraying or injecting before the completion of preparation.

Compounds of General Formulae 1 to 5 with or without isoflavones may be taken together with minerals, particularly, calcium compound so that the present agent exhibits its effects on calcium deposition in calcium-containing tissues as much as possible.

Therefore, it is preferable that minerals are added in the agent which is then advantageously incorporated in foods, cosmetics, or pharmaceuticals. Particularly, calcium chloride, calcium glycerophosphate, calcium gluconate, calcium lactate, calcium carbonate, calcium hydrogen phosphate, calcium dihydrogen phosphate, calcium hopantenate, calcium pantothenate, calcium fluoride, calcium thioglycollate, calcium sulfate, calcium silicate, calcium acetate, calcium L-aspartate, calcium citrate, calcium malate, and calcium succinate are illustrative for such calcium compound: These may be used in combination.

To improve the effects of the agent according to the present invention, it is preferable that minerals other than the above described calcium compounds, such as potassium, sodium, magnesium, manganese, phosphorus, iron, and zinc, are incorporated in the agent together with calcium compounds along with calcium compounds to give a desired mineral balance. Particularly, it is desirable to take magnesium together with calcium because magnesium compounds are effective in the prevention of hypercalcemia. An amount of magnesium compound in the agent of the present invention is equimole or less, desirably, 0.5 to 0.05 moles to one mole of calcium compound. Magnesium oxide, magnesium chloride, magnesium carbonate, or magnesium sulfate are illustrative for such a mineral.

Since minerals are easily insolubilized and altered for their assimilability in the intestine, one can much more effectively practice the present invention when he or she incorporates in the agent with a material which are mineral absorption-promoting activity which accelerate the absorption in the intestine and their assimilation in living bodies: Proteins or oligopeptides such as casein phosphopeptide, oligosaccharides such as isomaltoligosaccharide, fractooligosaccharide, xylooligosaccharide, lactosucrose, soybean oligosaccharide, $\alpha,\alpha$-trehalose, $\alpha,\beta$-trehalose, and lactose, organic acids such as lactic acid, acetic acid, citric acid, gluconic acid, and succinic acid are illustrative for such a substance and advantageously usable in the present invention.

To improve much more the effects of the agent according to the present invention, it is desirable to incorporate vitamins in the agent: active vitamin D, vitamin K, L-ascorbic acid, or derivatives thereof are illustrative for such a vitamin.

The following Experiments will explain the present invention.

Experiment 1
Searching from Variety of Organic Compounds by Measuring Alkaline Phosphatase Activity To increase number of osteoblastic cells having calcium-deposition activity is important for increasing bone mass. The compounds inducing the differentiation of mouse pre-osteoblastic cell MC3T3-E1 (RCB1126, Riken Gene Bank, Tokyo, Japan) were searched from variety of organic compounds known as plant ingredients by measuring alkaline phosphatase activity. The activity is at low level in pre-osteoblastic cells and at high level in osteoblastic cells differentiated form the pre-osteoblastic cells.

Culturing Mouse Pre-Osteoblastic Cells

Mouse pre-osteoblastic cell line MC3T3-E1 was suspended in $\alpha$-MEM medium (pH6.8) supplemented with 10 mM HEPES and 10 (v/v) % calf serum albumin (produced by Gibco BRL Company), which contains the ingredients listed in Table 7 to be concentration of $5\times10^4$ coils/ml, placed into 24 hole plate (Commercialized by Falcon Becton Dickinson and Company) by each 1 ml (5×14 cells) per one hole, and incubated at 37° C. in 5% $CO_2$ atmosphere to adhere to the plate bottom. After removing the medium from each hole, 20 mM of ethanol-dissolved each organic compound dissolved in ethanol, i.e., indomethacin (commercialized by Funakoshi, Co., Ltd., Tokyo, Japan) as a positive control, kaempferol (commercialized by Funakoshi, Co., Ltd., Tokyo, Japan), gallic acid (commercialized by Nacalai Tesque, Kyoto, Japan), coffeic acid (commercialized by Wako Pure Chemical Industries, Osaka, Japan), 4-Methylumbelliferone (commercialized by Wako Pure Chemical Industries, Osaka, Japan), caffein (commercialized by Wako Pure Chemical Industries, Osaka, Japan), β-carotene (commercialized by Sigma Corporation), glycyrrizin (commercialized by Katayama Chemical Industries, Co., Ltd., Osaka, Japan), menthol (commercialized by Wako Pure Chemical Industries, Osaka, Japan), theophylline (commercialized by Wako Pure Chemical Industries, Osaka, Japan), tocopherol (commercialized by Sigma Corporation), or vanillin (commercialized by Wako Pure Chemical Industries, Osaka, Japan), was pour into the each hole with 1 ml of $\alpha$-MEM medium supplemented with 10% (v/v) fetal calf serum and containing 10 mM β-glycerophosphate. Since final ethanol concentration in the medium is 0.2% (v/v), $\alpha$-MEM medium containing 0.2% (v/v) ethanol was prepared as a negative control. The cells were inoculated for eight days as changing the medium therewith to fresh medium with or without each sample per three days.

TABLE 7

| Ingredient | mg/l | Ingredient | mg/l |
| --- | --- | --- | --- |
| L-Alanine | 25 | L-Ascorbic Acid | 50 |
| L-Arginine | 105 | Biotin | 0.1 |
| L-Asparagine | 25 | Choline | 1 |
| L-Aspartic acid | 30 | Cyanocobalamin | 1.36 |
| L-Cysteine | 100 | Folic Acid | 1 |
| L-Cystine | 24 | Inositol | 2 |
| L-Glutamic acid | 75 | Nicotinamide | 1 |
| L-Glutamine | 292 | Pantothenic Acid | 1 |
| Glycine | 50 | Pyridoxal | 1 |
| L-Histidine | 31 | Riboflavin | 0.1 |
| L-Isoleucine | 52 | Thiamine | 1 |
| L-Leucine | 52 | Calcium Chloride | 200 |
| L-Lysine | 58 | Potassium Chloride | 400 |
| L-Methionine | 15 | Magnesium Chloride | 200 |
| L-Phenylalanine | 32 | Sodium Chloride | 6,800 |
| L-Proline | 40 | Sodium Bicarbonate | 2,000 |
| L-Serine | 25 | Sodium Dihydrogenphosphate | 150 |
| L-Threonine | 47.6 | Glucose | 1,000 |
| L-Tryptophan | 10 | Lipoic Acid | 0.2 |
| L-Tyrosine | 36 | Phenolsulfonphthalein | 10 |
| L-Valine | 46 | Sodium Pyruvate | 110 |

Measuring Alkaline Phosphatase Activity

Alkaline phosphatase activity was measured using "Alkaline Phospha B-Test Wako" (commercialized by Wako Pure Chemical Industries, Osaka, Japan) according with Kajii et al (Archives of Oral Biology, Vol. 44, pp. 233-241, (1999)). Briefly, to the above described mouse pre-osteoblastic cells washed with 1 ml of 0.25 M sucrose solution three times after removing the medium were added 0.45 ml of 50 mM carbonate salt buffer (pH9.8) containing 1 mM magnesium chloride and 50 mM sucrose and 0.05 ml of 3.4 mM disodium p-nitrophenyl phosphate in due course. The mixture was incubated at 25° C. for five minutes and admixed with 1.5 ml of 0.6N sodium hydroxide as a reaction terminator. Absorbance 405 nm of p-nitrophenol generated by alkaline phosphatase in the resulting mixture was measured, and the obtained values were used as values as alkaline phosphatase activity. Table 8 shows relative activities of alkaline phosphatase compared to negative control group added with only medium containing 0.2% (v/v) ethanol.

TABLE 8

| Organic compound | Relative Alkaline phosphatase activity (%) |
| --- | --- |
| 0.2% (v/v) Ethanol | 100 |
| Indomethacin | 142 |
| Kaempferol | 162 |
| Gallic Acid | 79 |
| Coffeic Acid | 97 |
| 4-Methylumbelliferone | 96 |
| Caffein | 100 |
| β-Carotene | 81 |
| Glycyrrizinic Acid | 97 |
| Menthol | 95 |
| Theophylline | 92 |
| Tocopherol | 100 |
| Vanillin | 89 |

Table 8 shows that kaempferol made alkaline phosphatase activity in mouse pre-osteoblastic cell line (MC3T3-E1) enhance more than indomethacin as a positive control. The result reveals that kaempferol enhances alkaline phosphatase activity in mouse pre-osteoblastic cells and has an activity of differentiating pre-osteoblastic cells into osteoblastic cells.

Experiment 2
Selecting from Variety of Organic Compounds by Measuring Calcium Deposition Activity Following Experiment 1 which investigates differentiating pre-osteoblastic cells into osteoblastic cells, some of organic compounds were investigated whether they actually enhance calcium deposition or not. Indomethacin (commercialized by Funakoshi, Co., Ltd., Tokyo, Japan) (positive control), kaempferol (commercialized by Funakoshi, Co., Ltd., Tokyo, Japan), hesperetin (commercialized by Funakoshi, Co., Ltd., Tokyo, Japan), gallic acid (commercialized by Nacalai Tesque, Kyoto, Japan), and coffeic acid (commercialized by Wako Pure Chemical Industries, Osaka, Japan) were selected as organic compounds. Mouse MC3T3-E1 cells were treated with 20 mM each above compound dissolved in 1 ml of α-MEM medium supplemented with 10% (v/v) fetal calf serum and containing 10 mM β-glycerophosphate. Since final ethanol concentration in the medium is 0.2% (v/v), α-MEM medium containing 0.2% (v/v) ethanol was prepared as a negative control. The cells were inoculated for eight days as changing the medium therewith to fresh medium with or without each sample per three days. The cells were applied to measure calcium deposition therein by usual alizarin red-S staining method. Briefly to the cells washed with 1 ml of Dulbecco phosphate buffer saline twice after removing the medium were added 1 ml of 50 (v/v) % ethanol aqueous solution and incubated for 10 minutes. After removing the 50 (v/v) % ethanol aqueous solution, the cells were incubated with 1 ml of distilled water for 10 minutes. After removing the water, the cells were applied with 1 ml of 1% (w/v) alizarin red-S solution, incubated for 10 minutes, and washed with 1 ml of distilled water for three times after removing alizarin red-S solution. Then, the calcium deposition amount was measured in a manner of judging red color on the plate bottom since deposited calcium was stained by the above treatment. The judgement criterion "+" means same strength of red color as a negative control (only medium containing 0.2% (v/v) ethanol), "+++" means same strength of red color as a positive control (indomethacin), and "++" means half strength of the positive control. The result is shown in Table 9.

TABLE 9

| Organic Compound | Calcium Deposition Amount |
| --- | --- |
| 0.2% (v/v) Ethanol (Negative Control) | + |
| Indomethacin | +++ |
| Kaempferol | +++ |
| Hesperetin | +++ |
| Gallic Acid | + |
| Coffeic Acid | + |

As a result of Table 9, kaempferol or hesperetin was judged as same calcium deposition amount with indomethacin as negative control. The result reveals kaempferol or hesperetin has the activity of enhancing calcium deposition of pre-osteoblastic cells.

The results of Experiment 1 and 2 reveal that kaempferol has the activity of increasing alkaline phosphatase activity in pre-osteoblastic cells, i.e., the activity of differentiating pre-osteoblastic cells into osteoblastic cell, and kaempferol or hesperetin has the activity of enhancing calcium deposition.

Experiment 3
Comparing Between Flavonoids

Other flavonoid compounds than kaempferol or hesperetin were investigated where they have the same effect or not.

Flavone (commercialized by Kanto Kagaku, Tokyo, Japan), apigenin (commercialized by Funakoshi, Co., Ltd., Tokyo, Japan), flavonol (commercialized by Tokyo Kasei Kogyo, Co., Ltd., Tokyo, Japan), quercetin (commercialized by Kanto Kagaku, Tokyo, Japan), kaempferol (commercialized by Funakoshi, Co., Ltd., Tokyo, Japan), rutin (commercialized by Kanto Kagaku, Tokyo, Japan), flavanone (commercialized by Kanto Kagaku, Tokyo, Japan), naringenin (commercialized by Ardrich Corporation), hesperetin (commercialized by Funakoshi, Co., Ltd., Tokyo, Japan), hesperidin (commercialized by Kanto Kagaku, Tokyo, Japan), chalcone (commercialized by Merk Corporation), fuloretin (commercialized by Sigma Corporation), catechin (commercialized by Sigma Corporation), ipriflavone (commercialized by Daito Corporation, Toyama, Japan), taxifolin (commercialized by Funakoshi, Co., Ltd., Tokyo, Japan), sulfuretin (commercialized by Funakoshi, Co., Ltd.; Tokyo, Japan), or cyanidin (commercialized by Funakoshi, Co., Ltd., Tokyo, Japan) was selected as test samples. Alkaline phosphatase activity was measured by the method of Experiment 1. Calcium deposition was measured by usual method using "Calcium C Test Wako" (commercialized by Wako Pure Chemical Industries, Osaka, Japan), briefly, cultured cells were washed with 1 ml of Dulbecco phosphate buffer saline three times after removing the medium. To the resultant was added 0.5 ml of 2N hydrochloric acid to resolve deposited calcium. To 5 μl of the resultant solution were added 0.5 ml of 0.88M monoethanolamine buffer (pH11) and 0.05 ml of 0.63 mM o-cresolphthalein complexone solution (binding to calcium ion to form chelate complex) containing 69 mM 8-quinolinol and mixed. Calcium amount per one hole of the plate was calculated by measuring absorbance 570 nm of the resultants and standardizing with a standard calcium solution. The judgement of alkaline phosphatase activity or calcium deposition amount of each sample was to calculate the relative activity or the relative calcium deposition amount to the negative control (only medium containing 0.2% (v/v) ethanol) and to compare each other. The result is shown in Table 10.

TABLE 10

| | Relative Alkaline Phosphatase Activity (%) | Relative Calcium Deposition Amount (%) |
|---|---|---|
| 0.2% (v/v) Ethanol | 100 | 100 |
| Flavone | 103 | 158 |
| Apigenin | 128 | 247 |
| Flavonol | 139 | 295 |
| Quercetin | 120 | 118 |
| Kaempferol | 162 | 305 |
| Rutin | 109 | 74 |
| Flavanone | 109 | 311 |
| Naringenin | 110 | 271 |
| Hesperetin | 116 | 289 |
| Hesperidin | 107 | 118 |
| Chalcone | 105 | 104 |
| Phloretin | 109 | 238 |
| Catechin | 118 | 247 |
| Ipriflavone | 114 | 263 |
| Taxifolin | 98 | 234 |
| Sulfuretin | 126 | 157 |
| Cyanidin | 115 | 216 |

As a result of Table 10, many of the flavonoid samples as an effective ingredient of the present invention demonstrated increasing calcium deposition amount. The result reveals that the effects on differentiating pre osteoblastic cells into osteoblastic cells and enhancing calcium deposition are common effect among flavones, flavonols, flavanones, flavanonols, anthocyanidins, flavanols, chalcones and aurones.

Experiment 4
Comparing the Enhancement of Alkaline Phosphatase Activity Among Kaempferol, Hesperetin, and Ipriflavone Kaempferol, hesperetin, or ipriflavone known as a curative of osteoporosis was selected as test samples and the enhancement of differentiating pre-osteoblastic cells into osteoblastic cells was compared. The experiment was performed by the method according to Experiment 1 except that culture day in the medium containing each sample was three, six or nine, and concentration of each sample was 5, 10 or 20 μM. Final ethanol concentration in the medium is 0.05% (v/v) when the concentration of test sample is 5 μM; 0.1% (v/v) when 10 μM; 0.2% (v/v) when 20 μM. As a negative control, mediums containing ethanol in the above concentration were prepared for calculating relative activity to the activity of each control. The result is shown in FIG. 1.

Figure 1:
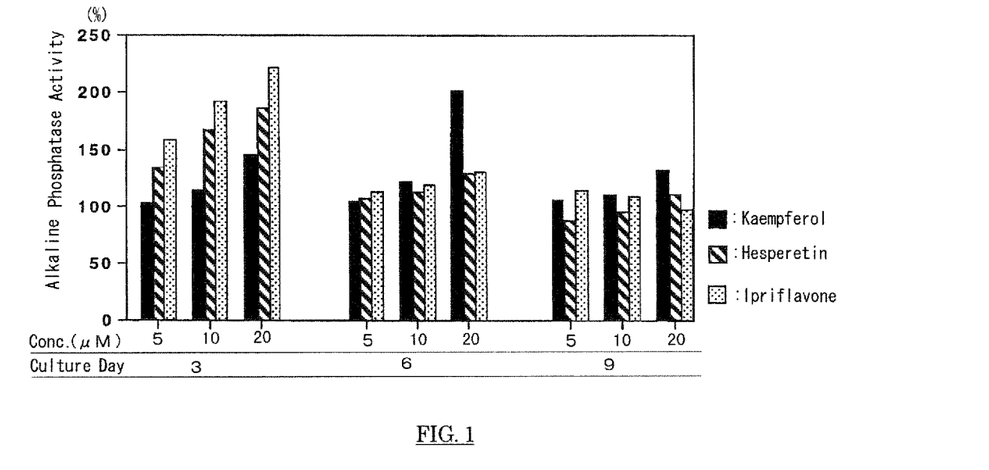
FIG. 1 shows daily courses of kaempferol, hesperetin and ipriflavone with different concentrations as determined for the effect of enhancing alkaline phosphatase activity.

As a result of FIG. 1, 20 μM kaempferol demonstrated the delayed enhancement of alkaline phosphatase activity at sixth day, and hesperidin demonstrated the remarkable enhancement of alkaline phosphatase activity at third day. The result reveals that kaempferol or hesperetin equally enhances the alkaline phosphatase activity of mouse pre-osteoblastic cell line (MC3T3-E1) with ipriflavone known as an osteoporosis curative.

Experiment 5
Comparing the Enhancement of Calcium Deposition Between Kaempferol and Ipriflavone The enhancement of calcium deposition between kaempferol and ipripfavone were compared. Test samples and their adding manner were same as Experiment 4. Calcium deposition amount was measured by usual method using "Calcium C Test Wako" (commercialized by Wako Pure Chemical Industries, Osaka, Japan); briefly, cultured cells were washed with 1 ml of Dulbecco phosphate buffer saline three times after removing the medium. To the resultant was added 0.5 ml of 2N hydrochloric acid to resolve deposited calcium. To 5 μl of the resolving solution were added 0.5 ml of 0.88M monoethanolamine buffer (pH11) and 0.05 ml of 0.63 mM o-cresolphthalein complexone solution (binding to calcium ion to form chelate complex) containing 69 mM 8-quinolinol and mixed, Calcium amount per one hole of the plate was calculated by measuring absorbance 570 nm of the resultants and standardizing with a standard calcium solution. The result of comparison with kaempferol and ipriflavone was shown in FIG. 2. The result of only ethanol treatment as a negative control is also shown in FIG. 2.

Figure 2:
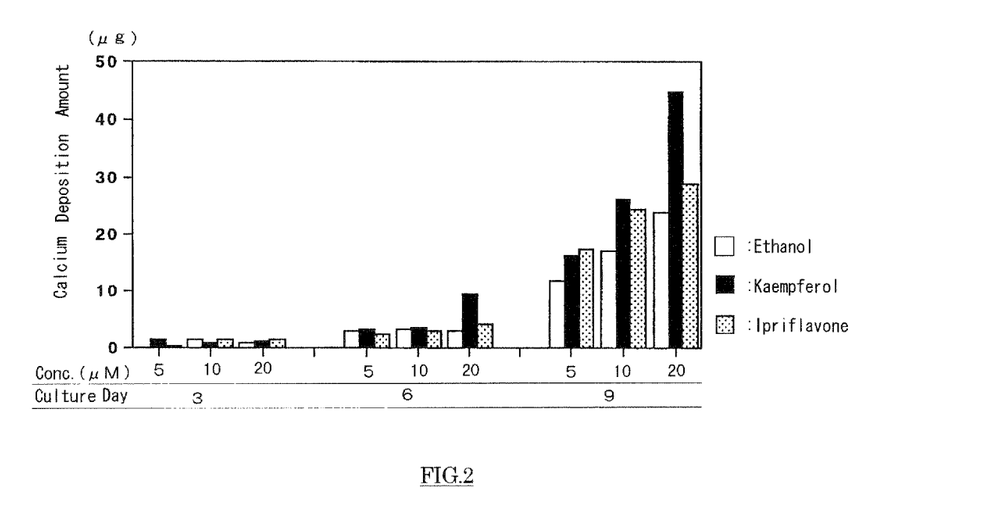
FIG. 2 shows daily courses of ethanol, kaempferol and ipriflavone with different concentrations as determined for the effect of enhancing calcium deposition.

As a result of FIG. 2, kaempferol demonstrated higher enhancement of calcium deposition than ipriflavone.

The results of Experiment 4 and 5 reveal that kaempferol or hesperetin exerts the effects on enhancement of alkaline phosphatase activity and calcium deposition in mouse pre-osteoblastic cell as well as ipriflavone known as an osteoporosis curative, and has the effect on strengthening calcium-containing tissues.

Figure 3:
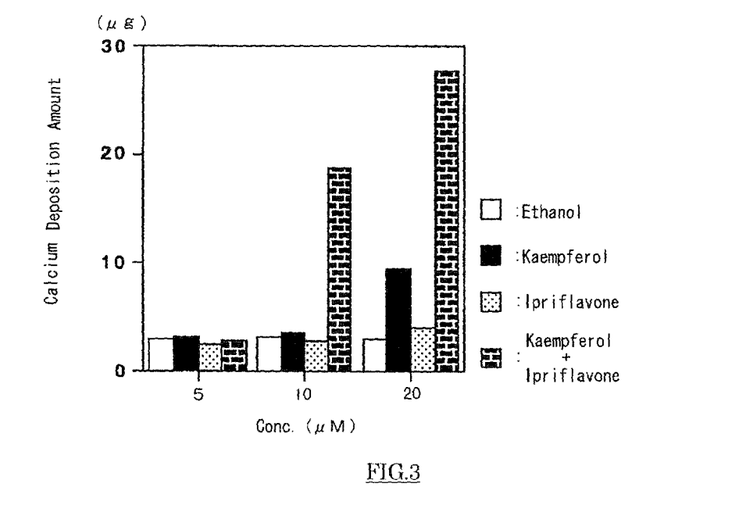
FIG. 3 shows an evidence for combination effect of kaempferol and ipriflavone with different concentrations as determined for the effect of enhancing calcium deposition.
Figure 4:
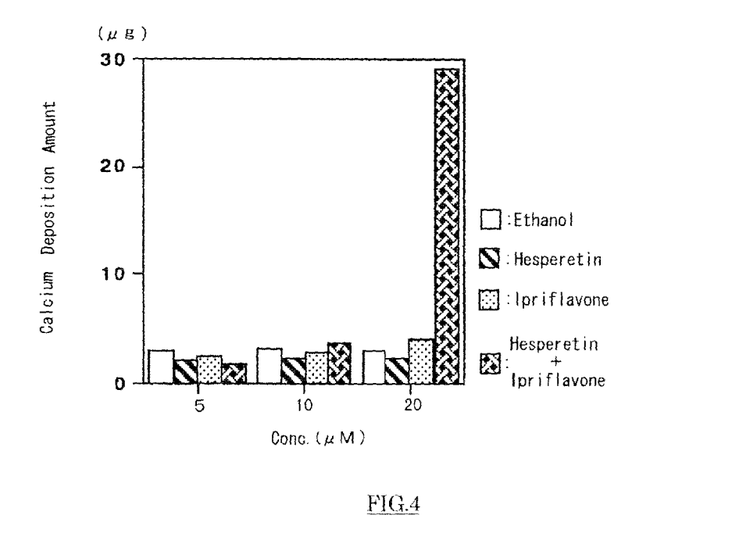
FIG. 4 shows an evidence for combination effect of hesperetin and ipriflavone with different concentrations as determined for the effect of enhancing calcium deposition.

Experiment 6
The Enhancement of Calcium Deposition by Kaempferol or Hesperetin in Combination with Ipriflavone Kaempferol or hesperetin in combination with ipriflavone, or a kind of isoflavones, was investigated whether to enhance calcium deposition or not. Methods for preparing samples and culturing the cells were the same method described in Experiment 1 except culturing the cells for five days, Method for measuring calcium was the same method described in Experiment 3 and 5. Final ethanol concentration of the medium containing each sample was adjusted as same concentration. FIG. 3 shows the result of 5, 10 or 20 μM kaempferol (single), 5, 10 or 20 μM ipriflavone (single), or 5, 10 or 20 μM kaempferol and ipriflavone (combination). FIG. 4 shows the result of 5, 10 or 20 μM kaempferol (single), 5, 10 or 20 μM ipriflavone (single), or 5, 10 or 20 μM kaempferol and ipriflavone (combination).

As the results of FIGS. 3 and 4, either of kaempferol or hesperetin in combination with ipriflavone demonstrated a remarkable effect on enhancing the calcium deposition than each case of the single use, and then, a synergy effect was confirmed.

Experiment 7
Enhancing Calcium Deposition in Rat Femur and Tibia

The experiment was performed using six three-weeks-aged female Wister rats per one group. The rats were fed with high sucrose feeding stuff containing ingredients listed Table 11 (In the Table, each value means "weight %".) and one part by weight of each test sample; hesperetin (commercialized by Funakoshi, Co., Ltd., Tokyo, Japan), quercetin (commercialized by Tokyo Kasei Kogyo, Co., Ltd., Tokyo, Japan), α-glycosyl hesperidin (product name "αG HESPERIDINE", commercialized by Hayashibara Shoji Inc., Okayama, Japan), α-glycosyl rutin (product name "αG RUTIN P", commercialized by Hayashibara Shoji Inc., Okayama, Japan), or ipriflavone (commercialized by Daito Corporation, Toyama, Japan) (positive control). As a negative control, rats fed with feedstuff containing one part by weight of sucrose replacing test sample were prepared. The rats were allowed to freely take water. The rats were killed after eight weeks, and then, their femurs and tibias were excised. Each femur or tibia dried at 100° C. for about six hours was measured by electric even balance for high precision analysis (product name "HA180M/12QM", commercialized by A & D Co, Ltd., Tokyo, Japan), and then, each bone was placed into a crucible and burned in an incinerator at 950° C. for six hours. The cinerary resultant was resolved in hydrochloric solution and provided for measuring calcium amount by atomic absorption photometer. Calcium amount per one dried bone was calculated and compared each other. The result is shown in Table 12.

TABLE 11

| Ingredient of Feeding Stuff (weight %) | Test Group | | | | | |
|---|---|---|---|---|---|---|
| | Hesperetin | Quercetin | α-Glycosyl Rutin | α-Glycosyl Hesperidin | Ipriflavone | None (Control Group) |
| Flavonoids (Samples) | 0.5 | 0.5 | 1.25 | 1.25 | 0.5 | 0 |
| Corn Starch | 14.5 | 14.5 | 13.75 | 13.75 | 14.5 | 15 |
| Sucrose | | | 50 | | | |
| Casein | | | 20 | | | |
| Cellulose Powder | | | 5 | | | |
| Corn Oil | | | 5 | | | |
| Minerals | | | 3.5 | | | |
| Vitamins | | | 1.2 | | | |
| Methionine | | | 0.3 | | | |

TABLE 12

| Sample | | Dried Bone Mass (g) | Calcium Content Per One Dried Bone (mg) | Remark |
|---|---|---|---|---|
| Hesperetin | Femur | 0.463 | 125.1 | The Present |
| | Tibia | 0.357 | 109.0 | Invention |
| Quercetin | Femur | 0.456 | 120.3 | The Present |
| | Tibia | 0.352 | 108.7 | Invention |
| α-Glycosyl Rutin | Femur | 0.439 | 119.9 | The Present |
| | Tibia | 0.343 | 107.7 | Invention |
| α-Glycosyl Hesperidin | Femur | 0.454 | 126.9 | The Present |
| | Tibia | 0.349 | 109.5 | Invention |
| Ipriflavone | Femur | 0.428 | 120.0 | Positive Control |
| | Tibia | 0.338 | 106.0 | |
| None | Femur | 0.427 | 116.4 | Negative Control |
| | Tibia | 0.331 | 105.9 | |

As the result shown in Table 12, all test samples more enhanced calcium deposition in both of femur and tibia equal to or more than ipriflavone as a negative control. While, glycosides such as hesperidin, α-glycosyl hesperidin, and α-glycosyl rutin also demonstrated increase of calcium deposition content, but the above glycosides did not demonstrate of alkaline phosphatase activity and calcium deposition in vitro. Therefore, flavonoids should be in an aglycon form for exerting the above effects, and are digested with inherent enzymes to be an active aglycon form removed saccharide part in the case of in vivo application.

Experiment 8
Acute Toxicity Test

The test was performed using five four-weeks-aged female Wister rats per one group. The 18-hours fasting rats were orally administered by constrained sonde with 10 ml/kg rat weight of the solution containing one part by weight of each test sample used in Experiment 3; flavone (commercialized by Kanto Kagaku, Tokyo, Japan), apigenin (commercialized by Funakoshi, Co., Ltd., Tokyo, Japan), flavonol (commercialized by Tokyo Kasei Kogyo, Co., Ltd., Tokyo, Japan), quercetin (commercialized by Kanto Kagaku, Tokyo, Japan), kaempferol (commercialized by Funakoshi, Co., Ltd., Tokyo, Japan), rutin (commercialized by Kanto Kagaku, Tokyo, Japan), flavanone (commercialized by Kanto Kagaku, Tokyo, Japan), naringenin (commercialized by Ardrich Corporation), hesperetin (commercialized by Funakoshi, Co., Ltd., Tokyo, Japan), hesperidin (commercialized by Kanto Kagaku, Tokyo, Japan), chalcone (commercialized by Merk Corporation), phloretin (commercialized by Sigma Corporation), catechin (commercialized by Sigma Corporation), ipriflavone (commercialized by Daito Corporation, Toyama, Japan), taxifolin (commercialized by Funakoshi Co., Ltd., Tokyo, Japan), sulfuretin (commercialized by Funakoshi, Co., Ltd., Tokyo, Japan), or cyanidin (commercialized by Funakoshi, Co., Ltd., Tokyo, Japan) and 25 parts by weight of 5 (w/v) % gum Arabic solution. The rats lived with constant temperature and humidity and were allowed to freely take feed and water. The rats were weighed and observed their condition and life-and-death for fourteen days from the administered day.

During two weeks, the rats administered with any test sample did not die and lose their weight. They were observed to have good appearance and no remarkable illness. Therefore, the compounds of General Formulae 1 to 5, which are used as effective ingredients in the present invention, are considered as more highly safe compounds.

Following examples explain the present invention

Example 1

Liquid Agent

Fifty parts by weight of ethanol dissolving one part by weight of "αG RUTIN", an α-glycosyl rutin commercialized by Hayashibara Shoji Inc., Okayama, Japan, and 0.1 part by weight of quercetin commercialized by Funakoshi, Co., Ltd., Tokyo, Japan, 5,000 parts by weight of water, 50 parts by weight of "TREHA", an α,α-trehalose commercialized by Hayashibara Shoji Inc., Okayama, Japan, three parts by weight of calcium lactate, 1.5 parts by weight of magnesium chloride, and 10 parts by weight of casein phosphopeptide were admixed and dissolved to obtain a liquid agent for strengthening calcium-containing tissues.

Since the product is easily taken, contains assimilable calcium, and has the activity of keeping and strengthening calcium-containing tissues, it can be advantageously used for treating and preventing osteoporosis or bone break.

Example 2

Liquid Agent

Fifty parts by weight of ethanol dissolving one part by weight of "αG HESPERIDIN PA", an α-glycosyl hesperidin commercialized by Hayashibara Shoji Inc., Okayama, Japan and 0.1 part by weight of hesperetin commercialized by Funakoshi, Co., Ltd., Tokyo, Japan, 5,000 parts by weight of water, 20 parts by weight of "TREHA", an α,α-trehalose commercialized by Hayashibara Shoji Inc., Okayama, Japan, five parts by weight of calcium chloride, 2.5 parts by weight of magnesium chloride, and 10 parts by weight of lactosucrose were admixed and dissolved to obtain a liquid agent for strengthening calcium-containing tissues.

Since the product is easily taken, contains assimilable calcium, and has the activity of keeping and strengthening calcium-containing tissues, it can be advantageously used for treating and preventing osteoporosis or bone break.

Example 3

Liquid Agent

Six parts by weight of sodium chloride, 0.3 parts by weight of potassium chloride, 0.2 parts by weight of calcium chloride 3.1 parts by weight of sodium lactate, 45 parts by weight of α,β-trehalose, and one part by weight of powdery α-glucosyl quercetin produced according to the method described in the Example A-2 of Japanese Patent Kokai No. 32,690/93, were dissolved in 1,000 parts by weight of water and purified by filtering out pyrogens. The resulting solution was filled in to a sterilized 25-ml ampule bottle to obtain an injection agent for strengthening calcium-containing tissues.

The product has an activity of keeping and strengthening calcium-containing tissues and can be advantageously used as an injection agent for treating and preventing osteoporosis or bone break, or accelerating the recovery from the diseases.

Example 4

Powdery Agent

One part by weight of "αG RUTIN H", an α-glycosyl rutin commercialized by Hayashibara Shoji Inc., Okayama, Japan, five parts by weight of soy bean isoflavone commercialized by Fuji Oil, Co., Ltd., Osaka, Japan, 1,000 parts by weight of "TREHA", an α,α-trehalose powder commercialized by Hayashibara Shoji Inc., Okayama, Japan, one part by weight of calcium lactate, and 0.5 parts by weight of magnesium sulfate were homogeneously admixed and dried to obtain a powdery agent for strengthening calcium-containing tissues.

Since the product easily resolves in water, contains a calcium and magnesium, and has the activity of strengthening calcium-containing tissues, it can be useful as an agent for treating and preventing osteoporosis or bone fracture or as a health food such as a health supplement and health-promoting food.

Example 5

Powdery Agent

One part by weight of "αG HESPERIDIN H", an α-glycosyl hesperidin commercialized by Hayashibara Shoji Inc., Okayama, Japan, 1,000 parts by weight of "TREHA", an α,α-trehalose powder commercialized by Hayashibara Shoji Inc., Okayama, Japan, one part by weight of calcium lactate, 0.5 parts by weight of magnesium sulfate and three parts by weight of "AA2G", an L-ascorbic acid-2-glucoside commercialized by Hayashibara Shoji Inc., Okayama, Japan were homogeneously admixed and dried to obtain a powdery agent for strengthening calcium-containing tissues.

Since the product easily resolves in water, contains a calcium and magnesium, and has the activity of strengthening calcium-containing tissues, it can be useful as an agent for treating and preventing osteoporosis or bone fracture or as a health food such as a health supplement and health-promoting food.

Example 6

Troche Agent

One part by weight of ethanol dissolving one part by weight of "αG HESPERIDIN PA", an α-glycosyl hesperidin commercialized by Hayashibara Shoji Inc., Okayama, Japan, and 0.1 part by weight of hesperetin commercialized by Funakoshi, Co., Ltd., Tokyo, Japan, two parts by weight of calcium lactate, 10 parts by weight of gum Arabic, 10 parts by weight of "TREHA", an α,α-trehalose powder commercialized by Hayashibara Shoji Inc., Okayama, Japan, five parts by weight of sucralose commercialized by San-Ei Gen F.F.I., Inc., Osaka, Japan, and three parts by weight of water were admixed well and formed by usual method to obtain a troche agent.

The product is stable and useful as a troche agent for keeping and increasing the calcium content in alveolar bones and teeth.

Example 7

Troche Agent

One part by weight of ethanol dissolving one part by weight of "αG RUTIN P", an α-glycosyl rutin commercialized by Hayashibara Shoji Inc., Okayama, Japan and 0.1 part by weight of quercetin commercialized by Funakoshi, Co., Ltd., Tokyo, Japan, two parts by weight of calcium lactate, 10 parts by weight of gum Arabic, 10 parts by weight of "TREHA", an α,α-trehalose powder commercialized by Hayashibara Shoji Inc., Okayama, Japan), two parts by weight of glycosyl-transferred stevia, and three parts by weight of water were admixed well and formed by usual method to obtain a troche agent.

The product is stable and useful as a troche agent for keeping and increasing the calcium content in alveolar bones and teeth.

Example 8

Health Supplement

Fifty-two parts by weight of "TREHA", an α,α-trehalose powder commercialized by Hayashibara Shoji Inc. Okayama, Japan, 40 parts by weight of corn starch, 0.5 parts by weight of "αG RUTIN P", an α-glycosyl rutin commercialized by Hayashibara Shoji Inc., Okayama, Japan, 0.5 parts by weight of "αG HESPERIDIN PA", an α-glycosyl hesperidin commercialized by Hayashibara Shoji Inc., Okayama, Japan, 0.1 part by weight of "AA2G", an L-ascorbic acid-2-glucoside commercialized by Hayashibara Shoji Inc., Okayama, Japan and calcium chloride, and 2.5 parts by weight of crystalline cellulose were admixed, kneaded as spraying water according to fluid bed granulation, pulverized, and sized to obtain a powder for tables. The powder were homogeneously mixed with two parts by weight of sucrose fatty acid ester as a lubricant tableted by tableting machine equipping an 11 mm in diameter of pestle to obtain a tablet agent (300 mg per one tablet).

Since the product is easily taken and disintegrated in alimentary canals, it can be useful as a health food such as a health supplement and health-promoting food for keeping and increasing calcium content.

Example 9

Drink Agent

One part by weight of "αG RUTIN P", an α-glycosyl rutin commercialized by Hayashibara Shoji Inc., Okayama, Japan, one part by weight of α-glycosyl narindin produced according to the method described in the Example A-2 of Japanese Patent Kokai No. 13,691/92, 20 parts by weight of grapefruit juice, two parts by weight of "TREHA", an α,α-trehalose powder commercialized by Hayashibara Shoji Inc., Okayama, Japan, two parts by weight of citric acid, one part by weight of "AA2G", an L-ascorbic acid-2-glucoside commercialized by Hayashibara Shoji Inc., Okayama, Japan, five parts by weight of isomerized sugar, six parts by weight of sea water, two parts by weight of calcium chloride, and 160 parts by weight of water were admixed, filled by each 100 ml into glass bottles, and sealed to obtain drink agent.

Since the product has a good flavor and taste, and has the effect of strengthening calcium-containing tissues, it is useful as a drink agent for treating and preventing osteoporosis or bone break.

Example 10

Drink Agent

One part by weight of "αG HESPERIDIN PA", an α-glycosyl hesperidin commercialized by Hayashibara Shoji Inc., Okayama, Japan, 50 parts by weight of apple juice, five parts by weight of isomerized sugar, two parts by weight of L-ascorbic acid, three parts by weight of "TREHA", an α,α-trehalose commercialized by Hayashibara Shoji Inc., Okayama, Japan, two parts by weight of sodium L-aspartate, and 35 parts by weight of water were admixed, filled and sealed by each 100 ml into glass bottles to obtain a drink agent.

Since the product has a good flavor and taste, and has the activity of strengthening calcium-containing tissues, it is useful as a drink agent for treating and preventing osteoporosis or bone break.

Example 11

Paste Agent

Forty-five parts by weight of dicalcium phosphate, three parts by weight of pullulan, 1.5 parts by weight of sodium laurylsulfate, 20 parts by weight of glycerin, 0.5 parts by weight of polyoxyethylene sorbitanlaurate, 10 parts by weight of sorbitol, seven parts by weight of maltitol, 12 parts by weight of a purified water, and one part by weight of ethanol containing 0.4 parts by weigh of "αG HESPERIDIN PA", an α-glycosyl hesperidin commercialized by Hayashibara Shoji Inc., Okayama, Japan, and 0.1 part by weight of hesperetin commercialized by Funakoshi, Co., Ltd., Tokyo, Japan, were admixed to obtain a tooth paste.

The product is stable and useful as toothpaste for keeping and increasing the calcium content in alveolar bones and teeth.

Example 12

Paste Agent

Forty-five parts by weight of dicalcium phosphate, three parts by weight of pullulan, 1.5 parts by weight of sodium laurylsulfate, 20 parts by weight of glycerin, 0.5 parts by weight of polyoxyethylene sorbitanlaurate, 10 parts by weight of sorbitol, seven parts by weight of maltitol, 12 parts by weight of a purified water, and one part by weight of ethanol containing 0.4 parts by weight of "αG RUTIN P", an α-glycosyl rutin commercialized by Hayashibara Shoji Inc., Okayama, Japan, and 0.1 part by weight of quercetin commercialized by Funakoshi, Co., Ltd., Tokyo, Japan, were admixed to obtain a tooth paste.

The product is stable and useful as toothpaste for keeping and increasing the calcium content in alveolar bones and teeth.

INDUSTRIAL APPLICABILITY

The agent for strengthening calcium-containing tissues, which comprises one or more compounds of General Formulae 1 to 5 or precursors thereof, demonstrates the strong effect on calcium deposition in pre-osteoblastic cells or osteoblastic cells, and further, it demonstrates the remarkably synergy effect in combination with isoflavones. Since it exerts the effects of inducing bone-growth and bone-formation and increasing bone mass, it can be taken in the form of a health food such as health supplement and health-promoting food, and also easily and comfortably taken in the form of daily foods and beverages. The agent of the present invention is useful for prevention of weakening bones and teeth of aged person and for treatment and prevention of osteoporosis, and is highly effective on prevention of delaying bone growth and bone formation caused by changing in dietary habits.

What is claimed is:

1. A treatment method for treating osteoporosis, comprising administering to an osteoporosis patient a mixture consisting essentially of, as active ingredients, through an oral or parenteral route,
   (1) ipriflavone,
   (2) hesperetin,
   (3) a calcium compound,
   (4) a magnesium compound, and
   (5) L-ascorbic acid-2-glucoside,
   the concentration of the combination of ipriflavone and hesperetin being at least 20 μM, and
   said mixture being administered to said patient in an amount of a daily dose of 0.1 to 500 mg/kg body weight.

2. The method of claim 1, wherein said calcium compound is selected from the group consisting of calcium chloride, calcium glycerophosphate, calcium gluconate, calcium lactate, calcium carbonate, calcium hydrogen phosphate, calcium dihydrogen phosphate, calcium hopantenate, calcium pantothenate, calcium fluoride, calcium thioglycollate, calcium sulfate, calcium silicate, calcium acetate, calcium L-aspartate, calcium citrate, calcium malate, and calcium succinate.

* * * * *